(12) United States Patent
Bramhe et al.

(10) Patent No.: US 12,429,866 B2
(45) Date of Patent: Sep. 30, 2025

(54) REMOTE SENSOR SYSTEM (71) Applicant: STEERING SOLUTIONS IP HOLDING CORPORATION, Saginaw, MI (US)

(72) Inventors: Mangesh Bramhe, Flint, MI (US); Eric D. Pattok, Frankenmuth, MI (US); Travis L. Palmer, Frankenmuth, MI (US)

(73) Assignee: Steering Solutions IP Holding Corporation, Saginaw, MI (US)

( * ) Notice: Subject to any disclaimer, the term of this patent is extended or adjusted under 35 U.S.C. 154(b) by 988 days.

(21) Appl. No.: 17/036,289

(22) Filed: Sep. 29, 2020

(65) Prior Publication Data

US 2021/0109519 A1 Apr. 15, 2021

Related U.S. Application Data

(60) Provisional application No. 62/913,805, filed on Oct. 11, 2019.

(51) Int. Cl.
*G05D 1/00* (2024.01)
*F02D 41/18* (2006.01)
(Continued)

(52) U.S. Cl.
CPC ........... *G05D 1/0038* (2013.01); *F02D 41/18* (2013.01); *G01N 33/0027* (2013.01);
(Continued)

(58) Field of Classification Search
CPC ...... G01D 11/245; G01D 11/24; G01D 11/26; H05K 2201/10151; H05K 1/189;
(Continued)

(56) References Cited

U.S. PATENT DOCUMENTS 6,300,739 B1 * 10/2001 Ratliff ................... H02K 11/33
318/689
6,535,116 B1 * 3/2003 Zhou .................. B60C 23/0408
340/447
(Continued)

FOREIGN PATENT DOCUMENTS

CN 101849173 A 9/2010
CN 107870755 A 4/2018
(Continued)

OTHER PUBLICATIONS

Official Letter from the German Patent and Trademark Office for related German Patent Application No. 102020126342.2 dated Aug. 16, 2021, 6 page(s).

(Continued)

*Primary Examiner* — Lisa M Caputo
*Assistant Examiner* — Carter W Ferrell
(74) *Attorney, Agent, or Firm* — Dickinson Wright PLLC (57) ABSTRACT

A remote sensor for a vehicle includes a first retaining cup disposed on a first end of the remote sensor. The remote sensor also includes a second retaining cup disposed proximate the first retaining cup, the second retaining cup being configured to mate with the first retaining cup. The remote sensor also includes a sensing device disposed in an aperture defined by the second retaining cup, the sensing device being configured to measure at least one characteristic of the vehicle. The remote sensor also includes a flex PCB having a first end connected to the sensing device and a second end connected or coupled to a controller of the vehicle, wherein at least a portion of the first end of the flex PCB is retained by the first retaining cup and the second retaining cup.

19 Claims, 3 Drawing Sheets

(51) Int. Cl.
  *F02D 41/24* (2006.01)
  *G01N 21/17* (2006.01)
  *G01N 33/00* (2006.01)
  *H05K 1/11* (2006.01)
  *H05K 5/00* (2025.01)
(52) U.S. Cl.
  CPC .......... *H05K 1/118* (2013.01); *H05K 5/0026*
    (2013.01); *F02D 41/2474* (2013.01); *G01N 2021/1793* (2013.01)
(58) Field of Classification Search
  CPC ...... H05K 5/0026; H05K 1/118; H05K 1/147; H05K 1/028; H05K 1/181; H05K 2201/10121; B60R 16/023; B60R 11/00; H04N 23/51
  See application file for complete search history.

(56) References Cited

U.S. PATENT DOCUMENTS

| | | | |
|---|---|---|---|
| 2005/0192727 A1* | 9/2005 | Shostak | G07C 5/008 701/1 |
| 2007/0031137 A1* | 2/2007 | Bogdan | G02B 7/021 348/E5.025 |
| 2011/0222225 A1* | 9/2011 | Kessler | G08C 19/16 361/679.02 |
| 2012/0006907 A1* | 1/2012 | Niemann | B60H 1/00792 73/29.02 |
| 2012/0073386 A1* | 3/2012 | McDonald | B62D 6/10 73/862.09 |
| 2016/0109317 A1* | 4/2016 | Gilman | G01L 19/0092 29/890.035 |
| 2016/0161299 A1* | 6/2016 | Campbell | F16C 19/527 73/431 |
| 2017/0054881 A1 | 2/2017 | Conger et al. | |
| 2018/0370471 A1 | 12/2018 | Bracalente et al. | |
| 2021/0199476 A1* | 7/2021 | Kortlang | G01J 1/0242 |

FOREIGN PATENT DOCUMENTS

| | | |
|---|---|---|
| CN | 110001742 A | 7/2019 |
| DE | 102007001381 A1 | 8/2007 |
| DE | 112018003281 T5 | 7/2020 |
| JP | H06270824 A | 9/1994 |
| KR | 19980023041 U | 7/1998 |
| KR | 20190097758 A | 8/2019 |
| WO | 2009088437 A1 | 7/2009 |

OTHER PUBLICATIONS

CN Office Action for corresponding CN Application No. 202011086711.7 mailed Jun. 7, 2024, 10 pages and CN Search Report, 3 pgs.
CN Office Action for corresponding CN Application No. 202011086711.7 mailed Oct. 10, 2024, 9 pages and CN Search Report, 2 pgs.

* cited by examiner

REMOTE SENSOR SYSTEM

CROSS-REFERENCES TO RELATED APPLICATIONS

This patent application claims priority to U.S. Provisional Patent Application Ser. No. 62/913,805, filed Oct. 11, 2019, which is incorporated herein by reference in its entirety.

TECHNICAL FIELD

This disclosure relates to vehicles and in particular to remote sensor systems for vehicles.

BACKGROUND OF THE INVENTION

Vehicles, such as cars, trucks, sport utility vehicles, crossovers, mini-vans, or other suitable vehicles, typically use remote sensing systems to monitor various aspects of such vehicles. For example, a vehicle may include a remote sensor that measures or senses exhaust emissions, a remote sensor that measures engine torque, and various other remote sensors for measuring various other characteristics of the vehicle. A remote sensor typically includes a connector, a length of wire (e.g., typically multiple wires), and a rigid printed circuit board.

SUMMARY OF THE INVENTION

This disclosure relates generally to remote sensors for vehicles.

An aspect of the disclosed embodiments includes a remote sensor for a vehicle. The remote sensor may include a first retaining cup disposed on a first end of the remote sensor and a second retaining cup disposed proximate the first retaining cup, the second retaining cup being configured to mate with the first retaining cup. The remote sensor may also include a sensing device disposed in an aperture defined by the second retaining cup, the sensing device being configured to measure at least one characteristic of the vehicle. The remote sensor may also include a flexible printed circuit board having a first end connected to the sensing device and a second end connected to a controller of the vehicle.

Another aspect of the disclosed embodiments includes a remote sensor for a vehicle. The remote sensor may include a first retaining cup disposed on a first end of the remote sensor and a second retaining cup disposed proximate the first retaining cup, the second retaining cup being configured to fixedly mate with the first retaining cup. The remote sensor may also include a sensing device disposed in an aperture defined by the second retaining cup, the sensing device being configured to measure at least one characteristic of the vehicle. The remote sensor may also include a flexible printed circuit board having a first end and a second end connected to a controller of the vehicle, wherein at least a portion of the first end of the flexible printed circuit board is retained by the first retaining cup and the second retaining cup, and wherein the sensing device is disposed on the first end of the flexible printed circuit board.

Another aspect of the disclosed embodiments includes a remote sensor for a vehicle. The remote sensor may include a first retaining cup and a second retaining cup adapted to fixedly mate with the first retaining cup. The remote sensor may also include a sensing device disposed in an aperture defined by the second retaining cup, the sensing device being configured to measure at least one characteristic of the vehicle. The remote sensor may also include a flexible printed circuit board extending from the sensing device at a first end and a second end connected to a controller of the vehicle, wherein at least a portion of the first end of the flexible printed circuit board is retained by the first retaining cup and the second retaining cup.

These and other aspects of the present disclosure are disclosed in the following detailed description of the embodiments, the appended claims, and the accompanying figures.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

As described, Vehicles, such as cars, trucks, sport utility vehicles, crossovers, mini-vans, or other suitable vehicles, typically use remote sensing systems to monitor various aspects of such vehicles. For example, a vehicle may include a remote sensor that measures or senses exhaust emissions, a remote sensor that measures engine torque, and various other remote sensors for measuring various other characteristics of the vehicle. A remote sensor typically includes a connector, a length of wire (e.g., typically multiple wires), and a rigid printed circuit board.

Typical methodologies for remote sensing in a vehicle include a separate rigid printed circuit board (PCB) (e.g., such as a fire resistant (FR-4) PCB or other suitable rigid PCB), a respective wire harness, and three or more mounting screws for securing the PCB to a mounting location within the vehicle. Additionally, or alternatively, flexible PCB (flex PCB) torque sensors may be used to measure or sense torque, such as engine toque, of the vehicle. Such flex PCB torque sensors may require adhesive, heat staking, and the like to mount and use within the vehicle. Such typical remote sensing technologies may be relatively expensive to manufacture and install within the vehicle.

Accordingly, systems and apparatuses, such as those described herein, that include remote sensors and/or remote sensor systems that replace typical remote sensing technology arrangements and include a flex PCB, may be desirable. In some embodiments, the systems and apparatuses described herein may include a top end of a flex PCB held between two retaining plastic cups.

In some embodiments, the systems and apparatuses described herein may include an end of the flex PCB opposite the top end. The end opposite the top end may be connected or coupled to a controller of the vehicle. The systems and apparatuses described herein may advantageously avoid using existing rigid PCBs, wire harnesses, and mounting/location screws of typical remote sensing technologies.

The systems and apparatuses described herein may reduce a geometric stack, which may result in tighter (e.g., improved) control of an air-gap between the remote sensor and a motor shaft of the vehicle.

The systems and apparatuses described herein may reduce or eliminate the use of adhesives and/or heat staking in order to mount, connect, and/or use the remote sensors (e.g., when compared to typical remote sensing and flex PCB technologies).

The systems and apparatuses described herein may utilize an existing retention scheme used for bearing retention in a vehicle motor housing, which may allow for the systems and apparatuses described herein to connect to and/or operate in the vehicle without additional machined surfaces.

In some embodiments, the systems and apparatuses disclosed herein may include a remote sensor for a vehicle that may include a first retaining cup disposed on a first end of the remote sensor and a second retaining cup disposed proximate the first retaining cup, the second retaining cup being configured to mate with the first retaining cup. The remote sensor may also include a sensing device disposed in an aperture defined by the second retaining cup, the sensing device being configured to measure at least one characteristic of the vehicle. The remote sensor may also include a flexible printed circuit board having a first end connected to the sensing device and a second end connected to a controller of the vehicle.

In some embodiments, the sensing device includes a radio detection and ranging sensor. In some embodiments, the sensing device includes a light detection and ranging sensor. In some embodiments, the sensing device includes a sound navigation and ranging sensor. In some embodiments, the sensing device includes a torque sensor. In some embodiments, the sensing device includes an emissions sensor. In some embodiments, the at least one characteristic of the vehicle includes vehicle emissions of the vehicle. In some embodiments, the sensing device is configured to communicate, using the flexible printed circuit board, a signal indicating the at least one characteristic of the vehicle to the controller. In some embodiments, the controller is configured to, in response to receiving the at least one characteristic of the vehicle from the sensing device, generate an output. In some embodiments, at least a portion of the first end of the flexible printed circuit board is retained by the first retaining cup and the second retaining cup. In some embodiments, the second end of the flexible printed circuit board is connected to the controller via soldered connection. In some embodiments, the second end of the flexible printed circuit board is secured to the controller via a mechanical connection.

In some embodiments, the systems and apparatuses disclosed herein may include a remote sensor for a vehicle that may include a first retaining cup disposed on a first end of the remote sensor and a second retaining cup disposed proximate the first retaining cup, the second retaining cup being configured to fixedly mate with the first retaining cup. The remote sensor may also include a sensing device disposed in an aperture defined by the second retaining cup, the sensing device being configured to measure at least one characteristic of the vehicle. The remote sensor may also include a flexible printed circuit board having a first end and a second end connected to a controller of the vehicle, wherein at least a portion of the first end of the flexible printed circuit board is retained by the first retaining cup and the second retaining cup, and wherein the sensing device is disposed on the first end of the flexible printed circuit board.

In some embodiments, the sensing device includes an emissions sensor. In some embodiments, the at least one characteristic of the vehicle includes vehicle emissions of the vehicle. In some embodiments, the sensing device is configured to communicate, using the flexible printed circuit board, a signal indicating the at least one characteristic of the vehicle to the controller. In some embodiments, the controller is configured to, in response to receiving the at least one characteristic of the vehicle from the sensing device, generate an output. In some embodiments, the second end of the flexible printed circuit board is connected to the controller via soldered connection. In some embodiments, the second end of the flexible printed circuit board is secured to the controller via a mechanical connection.

In some embodiments, the systems and apparatuses disclosed herein may include a remote sensor for a vehicle that may include a first retaining cup and a second retaining cup adapted to fixedly mate with the first retaining cup. The remote sensor may also include a sensing device disposed in an aperture defined by the second retaining cup, the sensing device being configured to measure at least one characteristic of the vehicle. The remote sensor may also include a flexible printed circuit board extending from the sensing device at a first end and a second end connected to a controller of the vehicle, wherein at least a portion of the first end of the flexible printed circuit board is retained by the first retaining cup and the second retaining cup.

Figure 1:
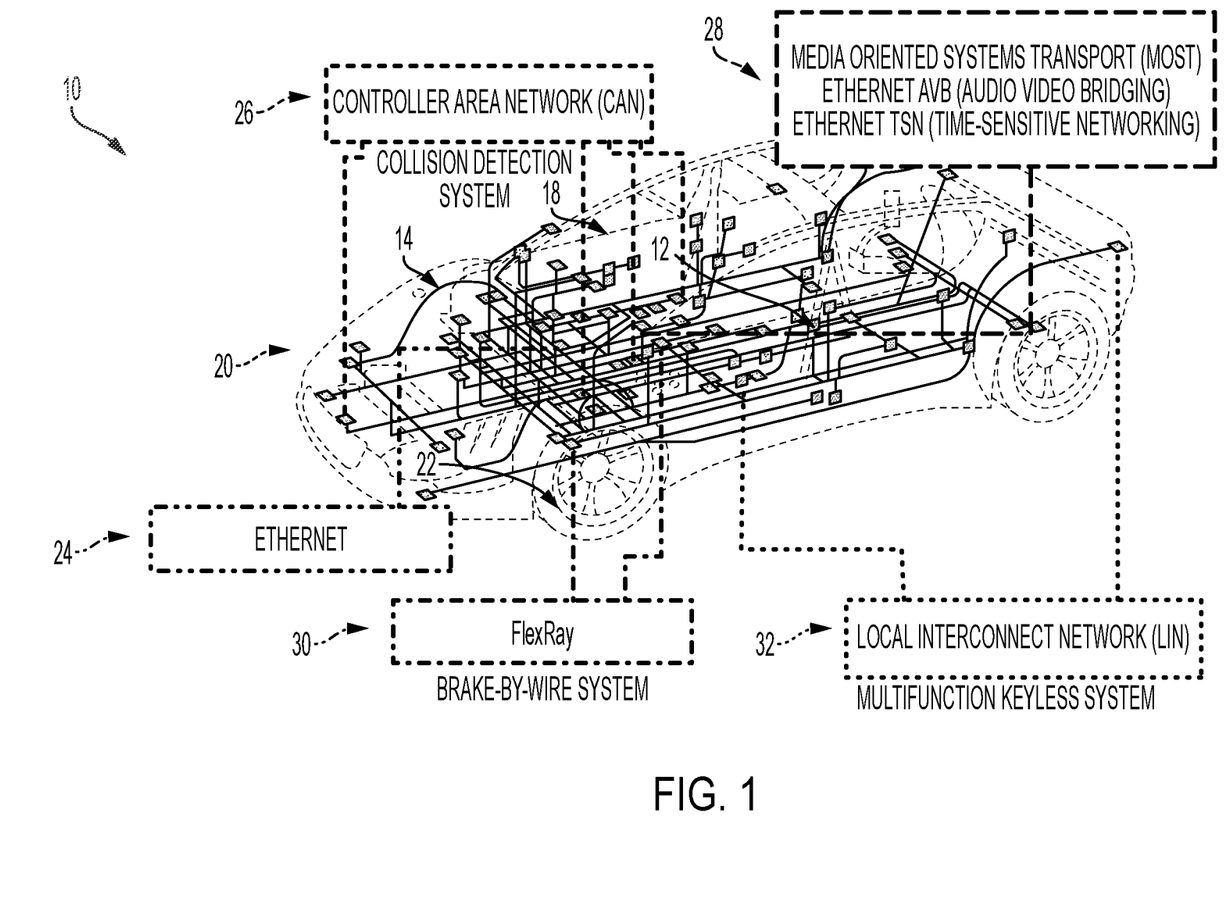
FIG. 1 generally illustrates a vehicle according to the principles of the present disclosure.

FIG. 1 generally illustrates a vehicle 10 according to the principles of the present disclosure. The vehicle 10 may include any suitable vehicle, such as a car, a truck, a sport utility vehicle, a mini-van, a crossover, any other passenger vehicle, any suitable commercial vehicle, or any other suitable vehicle. While the vehicle 10 is illustrated as a passenger vehicle having wheels and for use on roads, the principles of the present disclosure may apply to other vehicles, such as planes, boats, trains, drones, or other suitable vehicles The vehicle 10 includes a vehicle body 12 and a hood 14. A passenger compartment 18 is at least partially defined by the vehicle body 12. Another portion of the vehicle body 12 defines an engine compartment 20. The hood 14 may be moveably attached to a portion of the vehicle body 12, such that the hood 14 provides access to the engine compartment 20 when the hood 14 is in a first or open position and the hood 14 covers the engine compartment 20 when the hood 14 is in a second or closed position. In some embodiments, the engine compartment 20 may be disposed on rearward portion of the vehicle 10 than is generally illustrated.

The passenger compartment 18 may be disposed rearward of the engine compartment 20, but may be disposed forward of the engine compartment 20 in embodiments where the engine compartment 20 is disposed on the rearward portion of the vehicle 10. The vehicle 10 may include any suitable propulsion system including an internal combustion engine, one or more electric motors (e.g., an electric vehicle), one or more fuel cells, a hybrid (e.g., a hybrid vehicle) propulsion system comprising a combination of an internal combustion engine, one or more electric motors, and/or any other suitable propulsion system.

In some embodiments, the vehicle 10 may include a petrol or gasoline fuel engine, such as a spark ignition engine. In some embodiments, the vehicle 10 may include a diesel fuel engine, such as a compression ignition engine. The engine compartment 20 houses and/or encloses at least some components of the propulsion system of the vehicle 10. Additionally, or alternatively, propulsion controls, such as an accelerator actuator (e.g., an accelerator pedal), a brake actuator (e.g., a brake pedal), a steering wheel, and other such components are disposed in the passenger compartment 18 of the vehicle 10. The propulsion controls may be actuated or controlled by a driver of the vehicle 10 and may be directly connected to corresponding components of the propulsion system, such as a throttle, a brake, a vehicle axle, a vehicle transmission, and the like, respectively. In some embodiments, the propulsion controls may communicate signals to a vehicle computer (e.g., drive by wire) which in turn may control the corresponding propulsion component of the propulsion system. As such, in some embodiments, the vehicle 10 may be an autonomous vehicle.

In some embodiments, the vehicle 10 includes a transmission in communication with a crankshaft via a flywheel or clutch or fluid coupling. In some embodiments, the transmission includes a manual transmission. In some embodiments, the transmission includes an automatic transmission. The vehicle 10 may include one or more pistons, in the case of an internal combustion engine or a hybrid vehicle, which cooperatively operate with the crankshaft to generate force, which is translated through the transmission to one or more axles, which turns wheels 22. When the vehicle 10 includes one or more electric motors, a vehicle battery, and/or fuel cell provides energy to the electric motors to turn the wheels 22.

The vehicle 10 may include automatic vehicle propulsion systems, such as a cruise control, an adaptive cruise control, automatic braking control, other automatic vehicle propulsion systems, or a combination thereof. The vehicle 10 may be an autonomous or semi-autonomous vehicle, or other suitable type of vehicle. The vehicle 10 may include additional or fewer features than those generally illustrated and/or disclosed herein.

In some embodiments, the vehicle 10 may include an Ethernet component 24, a controller area network (CAN) bus 26, a media oriented systems transport component (MOST) 28, a FlexRay component 30 (e.g., brake-by-wire system, and the like), and a local interconnect network component (LIN) 32. The vehicle 10 may use the CAN bus 26, the MOST 28, the FlexRay Component 30, the LIN 32, other suitable networks or communication systems, or a combination thereof to communicate various information from, for example, sensors within or external to the vehicle, to, for example, various processors or controllers within or external to the vehicle. The vehicle 10 may include additional or fewer features than those generally illustrated and/or disclosed herein.

Figure 2:
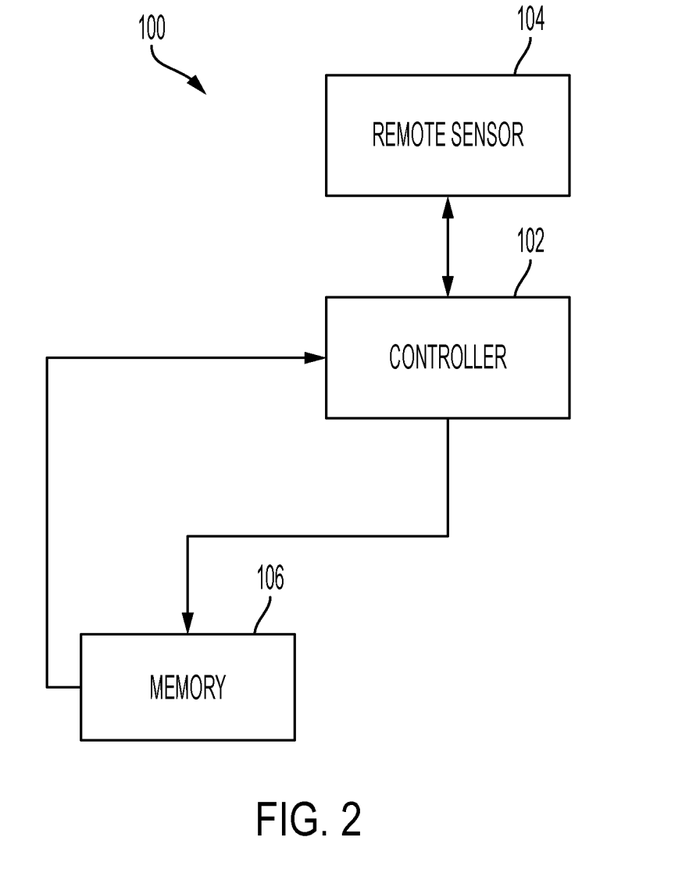
FIG. 2 generally illustrates remote sensor system according to the principles of the present disclosure.
Figure 3A:
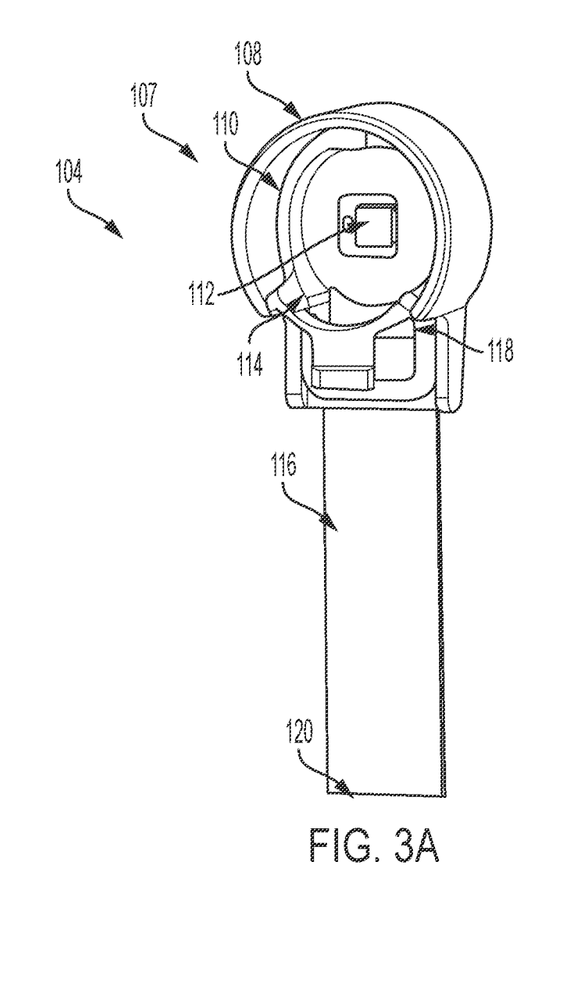
FIGS. 3A-3D generally illustrate a remote sensor according to the principles of the present disclosure.
Figure 3B:
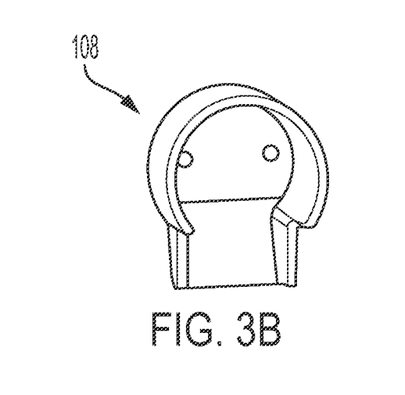
Figure 3C:
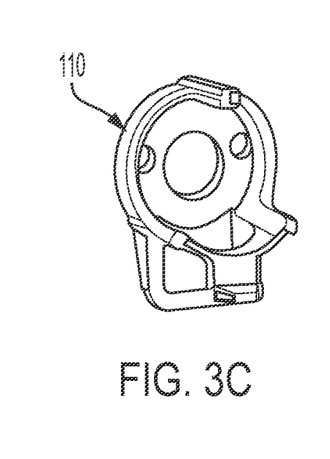
Figure 3D:
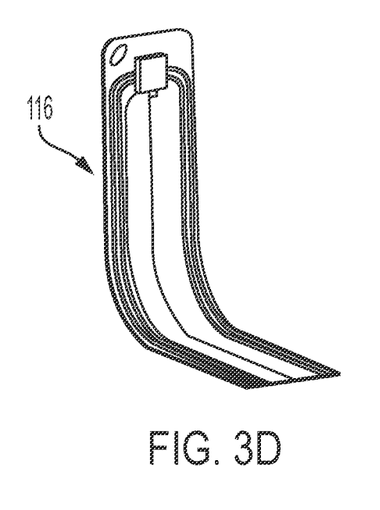

The vehicle 10 may include a remote sensor system 100 as is generally illustrated in FIG. 2. The system 100 may include a controller 102, a remote sensor 104, and a memory 106. The controller 102 may include any suitable controller, such as a vehicle electronic control unit, or any other suitable controller. The controller 102 may include a processor. The processor may include any suitable processor, such as those described herein. Additionally, or alternatively, the controller 102 may include any suitable number of processors in addition to or instead of the processor described herein. The memory 106 may comprise a single disk or a plurality of disks (e.g., hard drives), and includes a storage management module that manages one or more partitions within the memory 106. In some embodiments, memory 106 may include flash memory, semiconductor (solid state) memory or the like. The memory 106 may include Random Access Memory (RAM), a Read-Only Memory (ROM), or a combination thereof. The memory 106 may include instructions that, when executed by the processor, cause the processor to, at least, control various functions of the vehicle 10.

The controller 102 may be configured to receive input from the remote sensor 104. The remote sensor 104 may include any suitable sensor, such as a radio detection and ranging (radar) sensor, a light detection and ranging (LIDAR) sensor, a global positioning system (GPS) sensor, a sound navigation and ranging (sonar) sensor, a torque sensor, an emissions sensor, or other suitable sensor. The remote sensor 104 is configured to sense or monitor one or more vehicle characteristics of the vehicle 10. The vehicle characteristics may include vehicle position, vehicle emissions, engine torque, and so on. For example, the remote sensor 104 may include an emissions sensor disposed at or near an exhaust output of the vehicle 10 (e.g., and/or at or near any suitable mechanism of which the remote sensor 104 is configured to measure or sense characteristics). For example, the remote sensor 104 may sense or measure an amount of emissions (e.g., one or more of nitrogen oxide, non-methane organic gases, carbon monoxide, particulate matter, and formaldehyde). The remote sensor 104 may generate an output signal indicative of the sensed or measured emissions. The remote sensor 104 may communicate the output signal to the controller 102. The controller 102 may use the output signal to perform operations within the vehicle 10, to initiate functions or process within the vehicle 10, to generate indicators within the vehicle 10, to communicate to remotely located computing devices, and so on. It should be understood that, while the remote sensor 104 is described as sensing or measuring emissions, the remote sensor 104 may be configured t sensor or measure any suitable characteristic of any suitable mechanism or system of the vehicle 10.

FIGS. 3A-3D generally illustrate the remote sensor 104 according to the principles of the present disclosure. The remote sensor 104 may include a first end 107. A first retaining cup 108 is disposed at or near the first end 107 of the remote sensor 104. The remote sensor 104 includes a second retaining cup 110 disposed proximate the first retaining cup 108 at or near the first end 107. The second retaining cup 110 may be configured to mate with the first retaining cup 108. The remote sensor 104 includes a sensing device 112 disposed in an aperture 114 defined by the first retaining cup 108 and/or the second retaining cup 110. The sensing device 112 may be configured to sense and/or measure at least one vehicle characteristic of the vehicle, such as those described herein. The remote sensor 104 includes a cable 116. The cable 116 may include and/or be referred to as a flat flexible cable, a ribbon cable, a cable, a flexible PCB, a ribbon, and the like (e.g., the cable 116 may include a flex PCB).

The cable 116 includes a first end 118 connected to the sensing device 112. The cable 116 includes a second end 120 electrically connected to a controller of the vehicle 10. The controller of the vehicle may include the controller 102, a motor controller, or other suitable controller. The second end 120 of the cable 116 may be soldered to the controller of the vehicle or may be electrically connected or coupled to the controller of the vehicle in any suitable manner. In some embodiments, at least a portion of the first end 118 of the flex PCB 116 is retained by the first retaining cup 108 and the second retaining cup 110

In some embodiments, a remote sensor for a vehicle may include a first retaining cup disposed on a first end of the remote sensor and a second retaining cup disposed proximate the first retaining cup, the second retaining cup being configured to mate with the first retaining cup. The remote sensor may also include a sensing device disposed in an aperture defined by the second retaining cup, the sensing device being configured to measure at least one characteristic of the vehicle. The remote sensor may also include a flexible printed circuit board having a first end connected to the sensing device and a second end connected to a controller of the vehicle.

In some embodiments, the sensing device includes a radio detection and ranging sensor. In some embodiments, the sensing device includes a light detection and ranging sensor. In some embodiments, the sensing device includes a sound navigation and ranging sensor. In some embodiments, the sensing device includes a torque sensor. In some embodiments, the sensing device includes an emissions sensor. In some embodiments, the at least one characteristic of the vehicle includes vehicle emissions of the vehicle. In some embodiments, the sensing device is configured to communicate, using the flexible printed circuit board, a signal indicating the at least one characteristic of the vehicle to the controller. In some embodiments, the controller is configured to, in response to receiving the at least one characteristic of the vehicle from the sensing device, generate an output. In some embodiments, at least a portion of the first end of the flexible printed circuit board is retained by the first retaining cup and the second retaining cup. In some embodiments, the second end of the flexible printed circuit board is connected to the controller via soldered connection. In some embodiments, the second end of the flexible printed circuit board is secured to the controller via a mechanical connection.

In some embodiments, a remote sensor for a vehicle may include a first retaining cup disposed on a first end of the remote sensor and a second retaining cup disposed proximate the first retaining cup, the second retaining cup being configured to fixedly mate with the first retaining cup. The remote sensor may also include a sensing device disposed in an aperture defined by the second retaining cup, the sensing device being configured to measure at least one characteristic of the vehicle. The remote sensor may also include a flexible printed circuit board having a first end and a second end connected to a controller of the vehicle, wherein at least a portion of the first end of the flexible printed circuit board is retained by the first retaining cup and the second retaining cup, and wherein the sensing device is disposed on the first end of the flexible printed circuit board.

In some embodiments, the sensing device includes an emissions sensor. In some embodiments, the at least one characteristic of the vehicle includes vehicle emissions of the vehicle. In some embodiments, the sensing device is configured to communicate, using the flexible printed circuit board, a signal indicating the at least one characteristic of the vehicle to the controller. In some embodiments, the controller is configured to, in response to receiving the at least one characteristic of the vehicle from the sensing device, generate an output. In some embodiments, the second end of the flexible printed circuit board is connected to the controller via soldered connection. In some embodiments, the second end of the flexible printed circuit board is secured to the controller via a mechanical connection.

In some embodiments, a remote sensor for a vehicle may include a first retaining cup and a second retaining cup adapted to fixedly mate with the first retaining cup. The remote sensor may also include a sensing device disposed in an aperture defined by the second retaining cup, the sensing device being configured to measure at least one characteristic of the vehicle. The remote sensor may also include a flexible printed circuit board extending from the sensing device at a first end and a second end connected to a controller of the vehicle, wherein at least a portion of the first end of the flexible printed circuit board is retained by the first retaining cup and the second retaining cup.

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

The word "example" is used herein to mean serving as an example, instance, or illustration. Any aspect or design described herein as "example" is not necessarily to be construed as preferred or advantageous over other aspects or designs. Rather, use of the word "example" is intended to present concepts in a concrete fashion. As used in this application, the term "or" is intended to mean an inclusive "or" rather than an exclusive "or." That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an implementation" or "one implementation" throughout is not intended to mean the same embodiment or implementation unless described as such.

Implementations the systems, algorithms, methods, instructions, etc., described herein can be realized in hardware, software, or any combination thereof. The hardware can include, for example, computers, intellectual property (IP) cores, application-specific integrated circuits (ASICs), programmable logic arrays, optical processors, programmable logic controllers, microcode, microcontrollers, servers, microprocessors, digital signal processors, or any other suitable circuit. In the claims, the term "processor" should be understood as encompassing any of the foregoing hardware, either singly or in combination. The terms "signal" and "data" are used interchangeably.

As used herein, the term module can include a packaged functional hardware unit designed for use with other components, a set of instructions executable by a controller (e.g., a processor executing software or firmware), processing circuitry configured to perform a particular function, and a self-contained hardware or software component that interfaces with a larger system. For example, a module can include an application specific integrated circuit (ASIC), a Field Programmable Gate Array (FPGA), a circuit, digital logic circuit, an analog circuit, a combination of discrete circuits, gates, and other types of hardware or combination thereof. In other embodiments, a module can include memory that stores instructions executable by a controller to implement a feature of the module.

Further, in one aspect, for example, systems described herein can be implemented using a general-purpose computer or general-purpose processor with a computer program that, when executed, carries out any of the respective methods, algorithms, and/or instructions described herein. In addition, or alternatively, for example, a special purpose computer/processor can be utilized which can contain other hardware for carrying out any of the methods, algorithms, or instructions described herein.

Further, all or a portion of implementations of the present disclosure can take the form of a computer program product accessible from, for example, a computer-usable or computer-readable medium. A computer-usable or computer-readable medium can be any device that can, for example, tangibly contain, store, communicate, or transport the program for use by or in connection with any processor. The medium can be, for example, an electronic, magnetic, optical, electromagnetic, or a semiconductor device. Other suitable mediums are also available.

The above-described embodiments, implementations, and aspects have been described in order to allow easy understanding of the present disclosure and do not limit the present disclosure. On the contrary, the disclosure is intended to cover various modifications and equivalent arrangements included within the scope of the appended claims, which scope is to be accorded the broadest interpretation to encompass all such modifications and equivalent structure as is permitted under the law.

Having thus described the invention, it is claimed:

1. A remote sensor for a vehicle, comprising:
  a first retaining cup having a first circumferential characteristic and disposed on a first end of the remote sensor, wherein the first circumferential characteristic defines an outside circumference of the first retaining cup;
  a second retaining cup having a second circumferential characteristic configured to mate with the first circumferential characteristic of the first retaining cup and disposed proximate the first retaining cup, wherein the second circumferential characteristic defines an outside circumference of the second retaining cup;
  a sensing device disposed in an aperture defined by the second retaining cup, the sensing device being configured to measure at least one characteristic of the vehicle; and
  a flexible printed circuit board having a first end connected to the sensing device and retained by the first circumferential characteristic of the first retaining cup and the second circumferential characteristic of the second retaining cup and a second end connected to a controller of the vehicle,
  wherein the first retaining cup includes a hood portion configured to mate with the second retaining cup, wherein the hood portion defines a semi-circular arch that circumferentially extends from a portion of the first circumferential characteristic of the first retaining cup beyond the second circumferential characteristic of the second retaining cup, wherein the first retaining cup includes a recessed opening configured to mate with the second retaining cup, wherein the recessed opening extends from a portion of the first circumferential characteristic of the first retaining cup and defines an opening in the semi-circular arch of the hood portion, and
  wherein the second circumferential characteristic includes the aperture of the second retaining cup.

2. The remote sensor of claim 1, wherein the sensing device includes a radio detection and ranging sensor.

3. The remote sensor of claim 1, wherein the sensing device includes a light detection and ranging sensor.

4. The remote sensor of claim 1, wherein the sensing device includes a sound navigation and ranging sensor.

5. The remote sensor of claim 1, wherein the sensing device includes a torque sensor.

6. The remote sensor of claim 1, wherein the sensing device includes an emissions sensor.

7. The remote sensor of claim 6, wherein the at least one characteristic of the vehicle includes vehicle emissions of the vehicle.

8. The remote sensor of claim 1, wherein the sensing device is configured to communicate, using the flexible printed circuit board, a signal indicating the at least one characteristic of the vehicle to the controller.

9. The remote sensor of claim 1, wherein the controller is configured to, in response to receiving the at least one characteristic of the vehicle from the sensing device, generate an output.

10. The remote sensor of claim 1, wherein the second end of the flexible printed circuit board is connected to the controller via soldered connection.

11. The remote sensor of claim 1, wherein the second end of the flexible printed circuit board is secured to the controller via a mechanical connection.

12. A remote sensor for a vehicle, comprising:
  a first retaining cup having a first circumferential characteristic and disposed on a first end of the remote sensor, wherein the first circumferential characteristic defines an outside circumference of the first retaining cup;
  a second retaining cup having a second circumferential characteristic and configured to mate with the first circumferential characteristic of the first retaining cup and disposed proximate the first retaining cup, wherein the second circumferential characteristic defines an outside circumference of the second retaining cup;
  a sensing device disposed in an aperture defined by the second retaining cup, the sensing device being configured to measure at least one characteristic of the vehicle; and
  a flexible printed circuit board having a first end and a second end connected to a controller of the vehicle, wherein at least a portion of the first end of the flexible printed circuit board is retained by the first circumferential characteristic of the first retaining cup and the second circumferential characteristic of the second retaining cup, and the sensing device is disposed on the first end of the flexible printed circuit board,
  wherein the first retaining cup includes a hood portion configured to mate with the second retaining cup, wherein the hood portion defines a semi-circular arch that circumferentially extends from a portion of the first circumferential characteristic of the first retaining cup beyond the second circumferential characteristic of the second retaining cup, wherein the first retaining cup includes a recessed opening configured to mate with the second retaining cup, wherein the recessed opening extends from a portion of the first circumferential characteristic of the first retaining cup and defines an opening in the semi-circular arch of the hood portion, and
  wherein the second circumferential characteristic includes the aperture of the second retaining cup.

13. The remote sensor of claim 12, wherein the sensing device includes an emissions sensor.

14. The remote sensor of claim 13, wherein the at least one characteristic of the vehicle includes vehicle emissions of the vehicle.

15. The remote sensor of claim 12, wherein the sensing device is configured to communicate, using the flexible printed circuit board, a signal indicating the at least one characteristic of the vehicle to the controller.

16. The remote sensor of claim 12, wherein the controller is configured to, in response to receiving the at least one characteristic of the vehicle from the sensing device, generate an output.

17. The remote sensor of claim 12, wherein the second end of the flexible printed circuit board is connected to the controller via soldered connection.

18. The remote sensor of claim 12, wherein the second end of the flexible printed circuit board is secured to the controller via a mechanical connection.

19. A remote sensor for a vehicle, comprising:
- a first retaining cup having a first circumferential characteristic, wherein the first circumferential characteristic defines an outer circumference of the first retaining cup;
- a second retaining cup having a the first second circumferential characteristic and adapted to fixedly mate with the first circumferential characteristic of the first retaining cup, wherein the second circumferential characteristic defines an outer circumference of the second retaining cup;
- a sensing device disposed in an aperture defined by the second retaining cup, the sensing device being configured to measure at least one characteristic of the vehicle; and
- a flexible printed circuit board extending from the sensing device at a first end and a second end soldered to a controller of the vehicle, wherein at least a portion of the first end of the flexible printed circuit board is retained by the first circumferential characteristic of the first retaining cup and the second circumferential characteristic of the second retaining cup,
- wherein the first retaining cup includes a hood portion configured to mate with the second retaining cup, wherein the hood portion defines a semi-circular arch that circumferentially extends from a portion of the first circumferential characteristic of the first retaining cup beyond the second circumferential characteristic of the second retaining cup, wherein the first retaining cup includes a recessed opening configured to mate with the second retaining cup, wherein the recessed opening extends from a portion of the first circumferential characteristic of the first retaining cup and defines an opening in the semi-circular arch of the hood portion, and
- wherein the second circumferential characteristic includes the aperture of the second retaining cup.

* * * * *